United States Patent [19]
Simmons

[11] Patent Number: 5,622,499
[45] Date of Patent: Apr. 22, 1997

[54] METHOD OF MANUFACTURING A DENTAL ABUTMENT

[76] Inventor: William E. Simmons, 1225 Broken Sound Pkwy. NW., Boca Raton, Fla. 33487

[21] Appl. No.: 420,971

[22] Filed: Apr. 10, 1995

[51] Int. Cl.$^6$ .......................... A61C 13/12; A61C 13/225; A61C 8/00
[52] U.S. Cl. .............................................. 433/172; 433/173
[58] Field of Search .............................. 433/72, 75, 172, 433/173, 174, 175, 176

[56] References Cited

U.S. PATENT DOCUMENTS

| | | | |
|---|---|---|---|
| 5,215,460 | 6/1993 | Perry | 433/173 X |
| 5,221,204 | 6/1993 | Kruger et al. | 433/173 |
| 5,312,254 | 5/1994 | Rosenlicht | 433/173 |
| 5,334,024 | 8/1994 | Niznick | 433/173 |
| 5,350,297 | 9/1994 | Cohen | 433/173 X |
| 5,350,301 | 9/1994 | De Buck | 433/72 X |
| 5,473,662 | 12/1995 | Barish | 433/72 X |

*Primary Examiner*—Nicholas D. Lucchesi
*Attorney, Agent, or Firm*—M. K. Silverman

[57] ABSTRACT

A method of manufacturing a dental abutment to assure a desired in situ alignment of the dental abutment with a dental implant includes the steps of, firstly, providing a workpiece having a threaded recess corresponding to the length, diameter, pitch and material density of a coupling surface of an implant to be used in a dental procedure, this step followed by the step of rotating into the recess a coupling surface of the dental abutment to be secured in situ to the dental implant. The third step of the inventive method includes the tightening of the coupling surface of the abutment into the recess to a torque in the range of about 25 to about 35 newtons per centimeter which step is followed by the step of providing a radial surface of reference upon, and common to, both a non-threaded area of the abutment and a location proximal to the mouth of the recess of the workpiece. Resultingly, a desired degree of rotation and alignment of the abutment relative to said implant will be assured upon mutual alignment in situ of the radial surface of reference of the abutment and a dental implant provided with a reference corresponding to the radial reference on the workpiece.

3 Claims, 4 Drawing Sheets

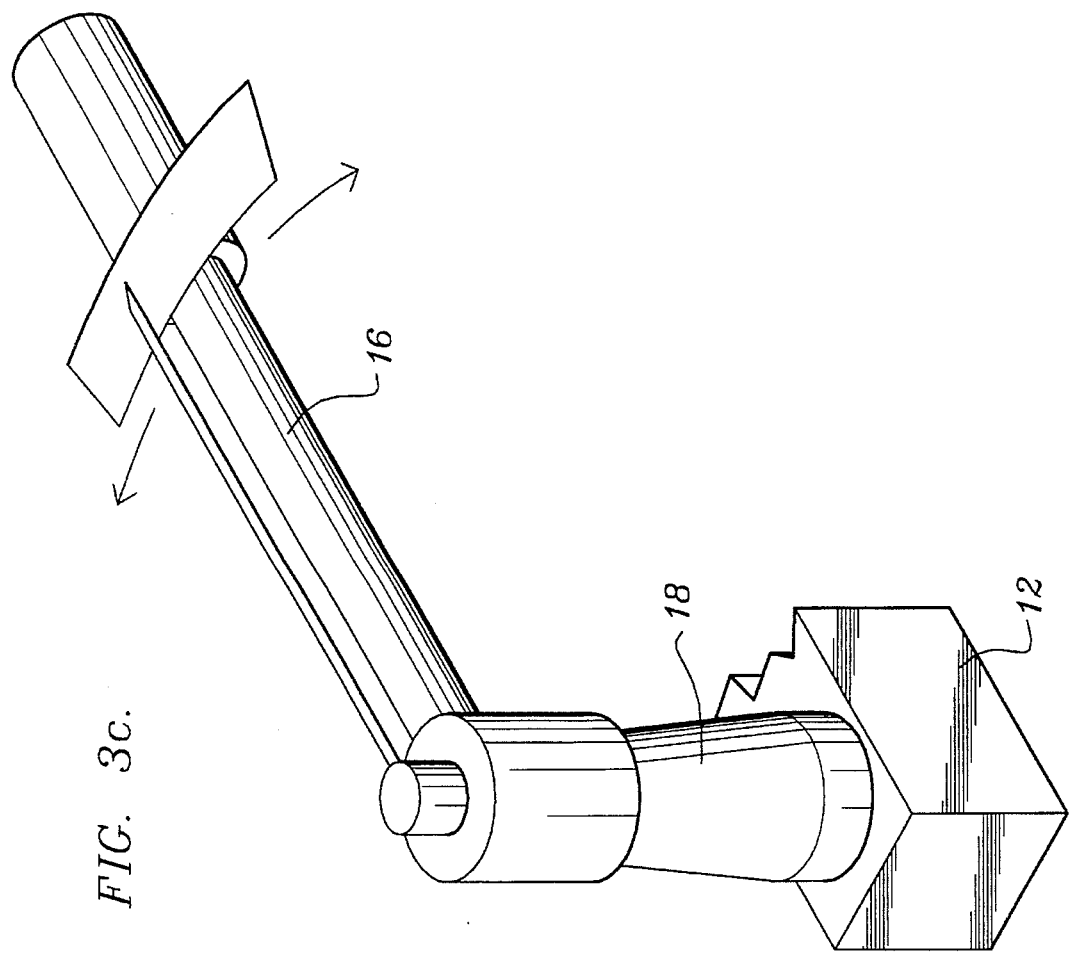
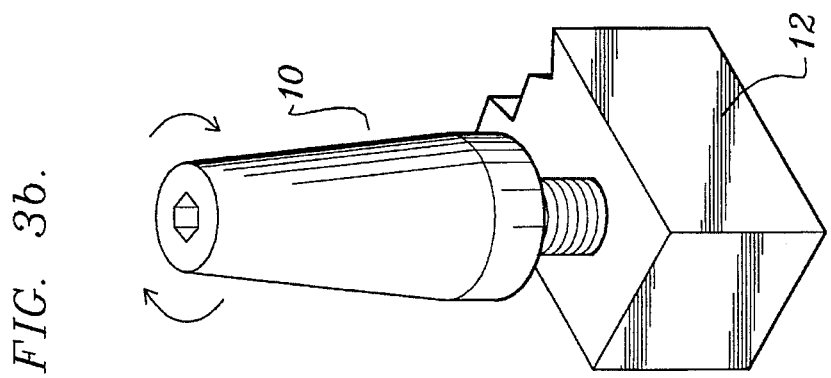
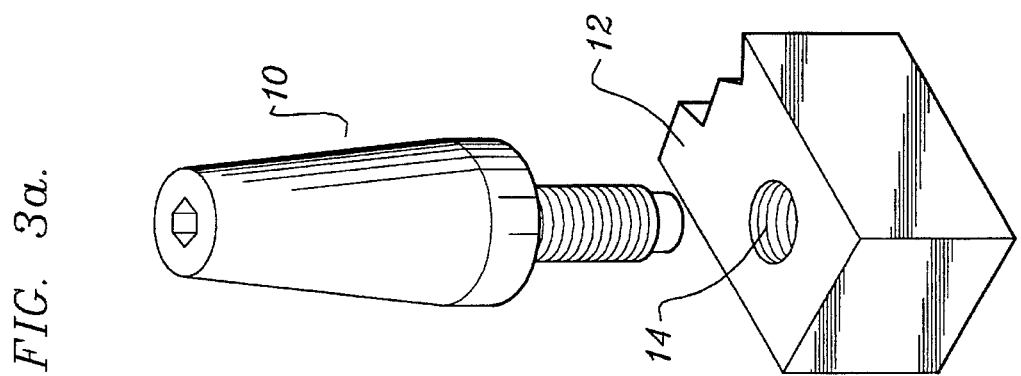

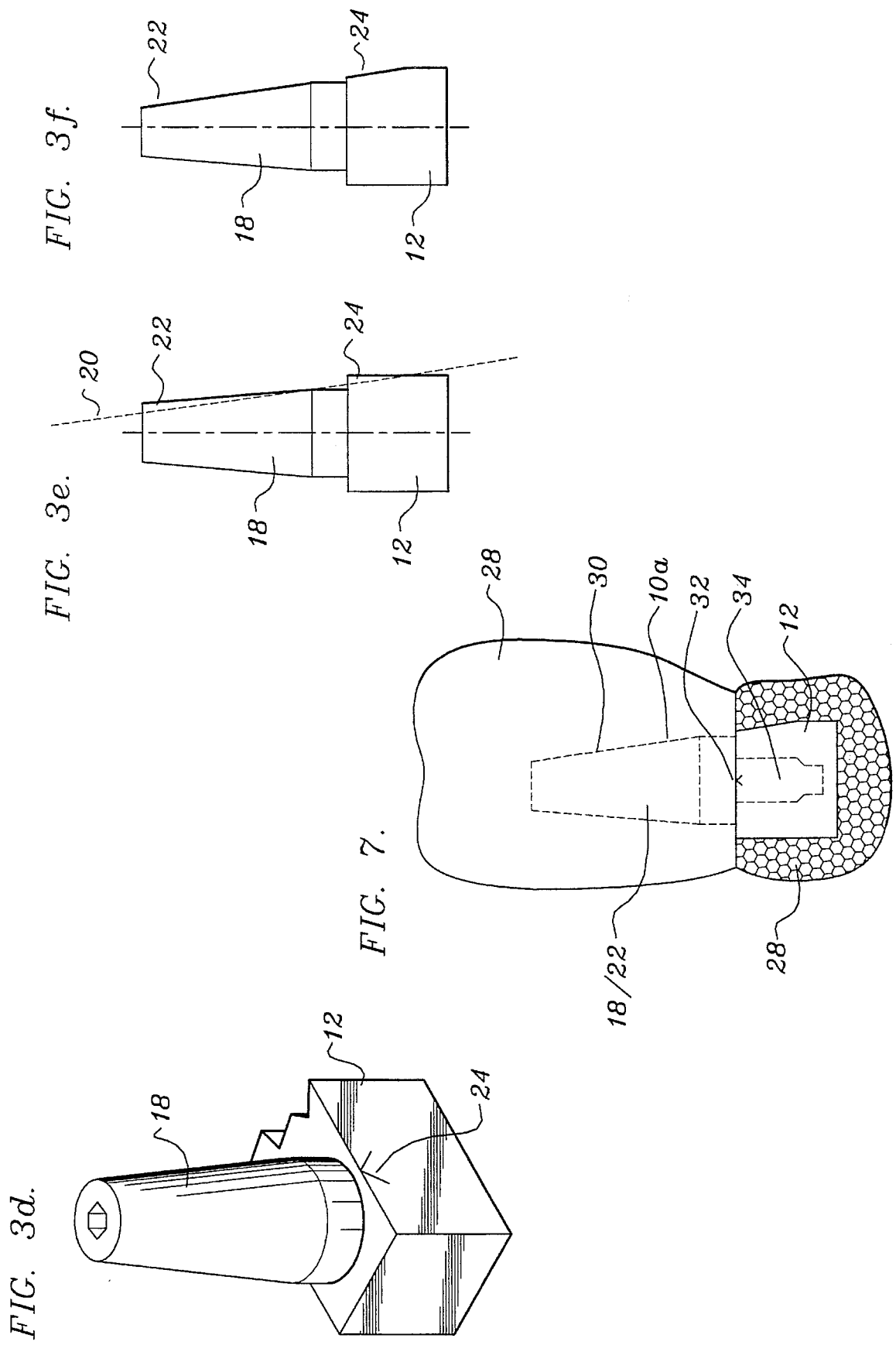

METHOD OF MANUFACTURING A DENTAL ABUTMENT

BACKGROUND OF THE INVENTION

The present invention relates to the art of manufacture of components used in dental implant systems and, more particularly, to a method of manufacture of a dental abutment usable in combination with a dental implant.

One of the difficulties associated with the practice of implant dentistry is that of proper alignment of the dental abutment (the element to which the dental prosthesis is attached) to the dental implant which has been surgically embedded within the jaw, maxilla, or mandible of the patient. More particularly, it is necessary, to assure optimal coupling between the abutment and the implant, to employ a standard parameter of tightening or torquing of the coupling member of the abutment relative to the he coupling recess of the implant. That is, in the absence of a standard torquing parameter, the possibility of under- or over rotation of the threaded interface between the abutment and the implant exists. The consequences thereof are apparent to one of skill in the art of implant dentistry, namely, that of a misalignment, even if microscopic, between the abutment and the implant and, thereby, a misalignment, or potential therefore between the dental prosthesis (which is associated with the abutment) and the implant. In such an event the mandible of the patient and the prosthesis may not operate in a synchronous or optional fashion and the life cycle of the prosthesis will be affected.

The instant invention presents a solution to the problem of in situ alignment of the abutment with the implant thru a novel method of manufacture of the abutment in a manner which assures that the implant dentist cannot misalign the abutment with the implant during an implant procedure.

There does not, to the knowledge of the inventor, exist any applicable prior art within the area of either implant dentistry or dentistry in general. Any art which, thereby, may exist in the general industrial arts is believed to be non-analogous to the invention as set forth herein.

SUMMARY OF THE INVENTION

The present invention is directed to a method of manufacturing a dental abutment to assure a desired in situ alignment of the dental abutment with a dental implant. The method more particularly includes the steps of, firstly, providing a workpiece having therein a threaded recess corresponding to the length, diameter, pitch and material density of a coupling surface of an implant to be used in a dental procedure, said step followed by the step of rotating into said recess a coupling surface of said dental abutment to secured in situ to the dental implant. The third step of the inventive method includes the tightening of said coupling surface of said implant into said recess to a torque in the range of about 25 to about 35 newtons per centimeter which step is followed by the step of providing a radial surface of reference upon, and common to, both a non-threaded area of said abutment and a location proximal to the mouth of said recess of said workpiece. Resultingly of the above, a desired degree of rotation and alignment of said abutment relative to said implant will be assured upon mutual alignment in situ of said radial surface of reference of said abutment and a dental implant provided with a reference corresponding to said radial reference workpiece.

It is, accordingly, an object of the invention to provide a method of manufacture of a dental abutment which will afford a means of positive location of the proper degree of rotation and, thereby, alignment, of a dental abutment relative to an implant during a dental procedure.

It is another object to provide a means by which the position of a dental prosthesis relative to the mandible or maxilla of the patient, in a dental implant procedure, can be assured thereby enhancing both product longevity and patient health.

It is a further object of the invention to provide a method of manufacture which will assure the proper radial location of an abutment after it is fully torqued relative to an implant or other fixed oral site.

It is a yet further object to provide a method of manufacture of a dental abutment that will assure exact replication, in the production process, of the coupling surface of the abutment.

It is a still further object of the invention to provide a means of production of a dental abutment that will enhance the force-loading which a resultant in situ dental implant system can successfully accept.

It is a still further to provide a method of production of a dental abutment that will render such an abutment interchangeable with other like abutments during clinical procedures.

The above and yet other objects and advantages of the present invention will become apparent from the hereinafter set forth Brief Description of the Drawings, Detailed Description of the Invention and Claims appended herewith.

BRIEF DESCRIPTION OF THE DRAWINGS

FIGS. 3A thru 3F are sequential views showing the steps of the inventive method.

FIG. 7 is a representation view showing the securement of a dental prosthesis onto an abutment manufactured in accordance with the present method.

DETAILED DESCRIPTION OF THE INVENTION

Figure 1:
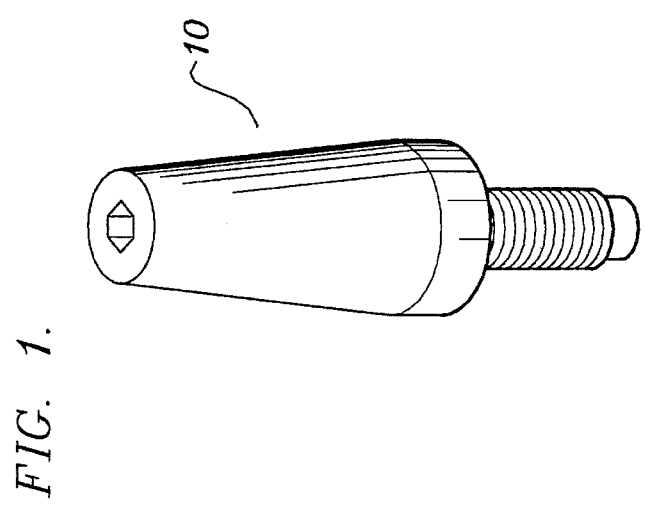
FIG. 1 is a perspective view of a dental abutment prior to the application of the steps of the present manufacturing method thereto.

With reference to the elevational view of FIG. 1 there is shown a dental abutment 10 after it has been machined into its general configuration but, however, prior to its processing in accordance with the present method of manufacture.

Figure 2:
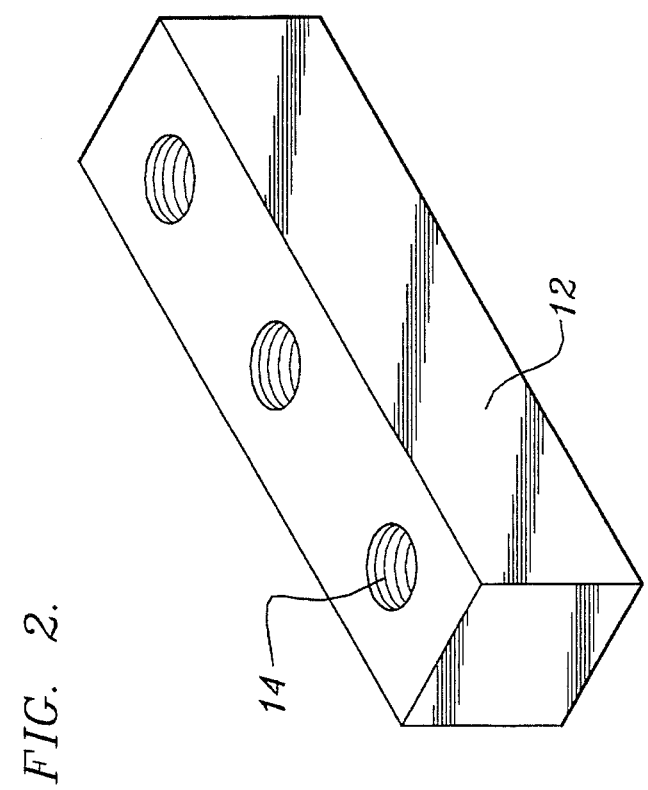
FIG. 2 is a perspective view of a workpiece which may be used in accordance with the present invention.

FIG. 2 shows, in schematic view, a workpiece 12 having therein a threaded recess 14 which corresponds in length, diameter, and pitch to a female coupling surface of a dental implant to be used in a dental procedure. It is also noted that workpiece 12 is formed of a material having a density which corresponds to that of the material of said dental implant, e.g., a titanium known as ASTM B 348 grade 5.

With reference to the schematic views of FIGS. 3A and 3B, the next step of the method of manufacture may be seen to include that of rotating into said recess 14 of a holding fixture 12 the above-described dental abutment 10. This step may be accomplished by rotation by hand of the abutment 10 relative to the fixture 12.

After the abutment has been hand-tightened into the recess 14, use is made of a torque wrench (see FIG. 3C) which has been calibrated to release head 18 of the workpiece 10 when the abutment has been tightened into the recess 14 to a torque parameter in the range of about 25 to about 35 newtons per centimeter.

Shown in FIG. 3D is the head 18 of the abutment 10 after it has been appropriately torqued into the fixture 12.

Shown in FIG. 3E is use of a cutting tool 20 which may take any of a number of forms, for example, a rotating tool such as a mill or a linear type of cutting tool. However, what is significant in the context of the instant method is that cutting tool 20 will provide to head 18 of the abutment 10 a surface of radial reference 22 which will correspond, in terms of radial location, to a radial reference 24 which, in a preferred embodiment, has been pre-formed on workpiece 12 at a position proximal to the mouth of the recess 14 of the workpiece. That is, after the abutment has been fully torqued into the recess of the workpiece, a tool 20 is employed to form a radial reference 22 which corresponds in radial position, relative to the longitudinal axis of the abutment 10, to radial reference of the workpiece 12. See FIG. 3F.

Figure 5:
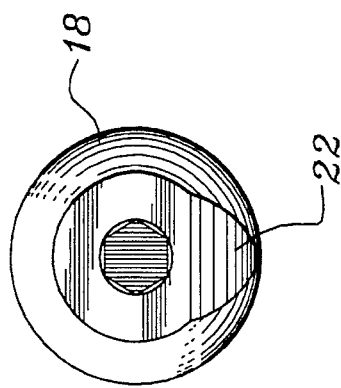
FIG. 5 is a top plan view of the abutment of FIG. 4.
Figure 6:
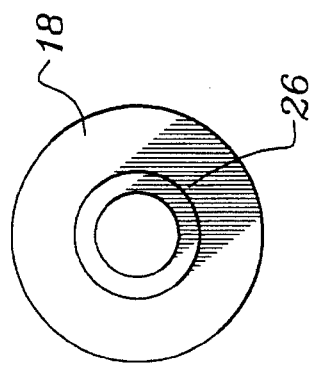
FIG. 6 is a bottom plan view of the abutment of FIG. 4.
Figure 4:
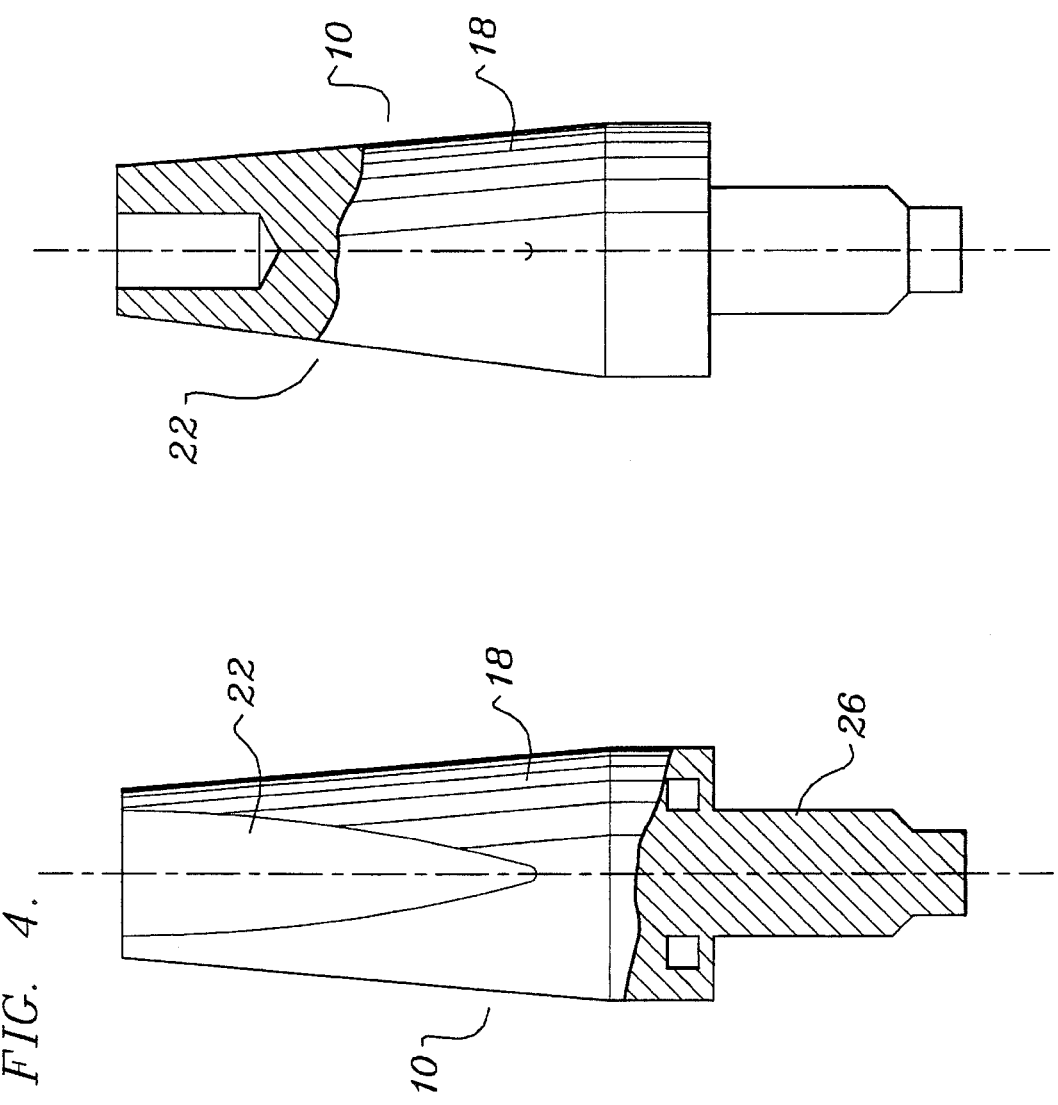
FIG. 4 is a side elevational view of an abutment after it has been radially indexed in accordance with the present method.

Resulting of the above method, there is provided an abutment 10A of the type shown in the respective side, top and bottom views of FIGS. 4 thru 6. Therein, as may be noted, said radial reference 22 upon the head 18 of abutment 10A takes the form of a flat diagonal surface having a progressively smaller area as it extends radially outwardly and longitudinally downwardly toward a threaded coupling surface 26 of the abutment 10A.

In the representational view of FIG. 7 there is shown the manner in which a dental prosthesis 28 is secured to the abutment 10A. Therein, it may be appreciated that the radial reference 22 can be employed to perform the additional function of assuring that the prosthesis 28 is positioned correctly relative to the abutment 10, by simply providing within the prosthesis a recess 30 which is complemental in geometry to the head 18 of the abutment inclusive of the radial reference 22. Accordingly, as may be seen in the view of FIG. 7, the radial reference performs the dual function of indicating to the dentist that a proper torquing of the abutment relative to the implant has occurred when indexing surface 22 is aligned with an indicator 32, or the like, upon the in situ implant 34, while also assuring proper positioning of the prosthesis 28 by reason of the complemental relationship between recess 30 thereof and head 18 (inclusive of surface 22) of the abutment 10A. As such, a desired degree of rotation and alignment of the abutment relative to the implant will be assured by virtue of a mutual in situ alignment of radial surface 22 and indicator 32 of the implant 34.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

Having thus described my invention what I claim as new, useful and non-obvious and, accordingly, secure Letters Patent of the United States is:

1. Method of manufacturing a dental abutment to assure a desired in situ alignment of the dental abutment with a dental implant, the method comprising the steps of:

(a) providing a workpiece having therein a threaded recess corresponding to the length, diameter, pitch and material density of a coupling surface of the dental implant to be used in a dental procedure said recess having a mouth;

(b) rotating into said recess a coupling surface of said dental abutment to be secured in situ to said dental implant said abutment having a non-threaded surface;

(c) tightening said coupling surface of said dental abutment into said recess to a torque in the range of about 25 to about 35 newtons per centimeter; and (d) providing a surface of radial reference upon, and common to, both said non-threaded area of said abutment and a location, proximal to said mouth of said recess of said workpiece, whereby a desired degree of rotation and alignment of said abutment relative to said implant will be assured upon mutual alignment in situ of said surface radial of reference of said abutment and a dental implant provided with a reference corresponding to said radial reference of said workpiece.

2. A method of manufacturing a dental abutment to assure desired in situ alignment of the dental abutment with the dental implant, the method comprising the steps of:

(a) providing a workpiece having a material density of the dental implant to be used in a dental procedure and providing within said workpiece a threaded recess corresponding in length, diameter and pitch to that of a coupling surface of said dental implant;

(b) providing upon said workpiece a radial reference relative to the longitudinal axis of said recess;

(c) rotating into said recess a coupling surface of said dental abutment to be secured in situ to said dental implant;

(d) tightening said coupling surface of said dental abutment into said recess to a torque in the range of about 25 to about 35 newtons per centimeter; and (e) providing a surface of radial reference upon a non-threaded area of said abutment which is radially aligned with said radial reference on said workpiece, whereby a desired degree of rotational alignment of said abutment relative to said implant will be assured upon mutual alignment in situ of said surface of reference of said abutment and a dental implant provided with a reference corresponding to said radial reference upon said workpiece.

3. The method of claim 2 further comprising the step of:

furnishing a dental prosthesis to be used with said abutment, having a recess complemental to said non-threaded area of the abutment.

* * * * *